(12) United States Patent
Mathad et al.

(10) Patent No.: US 8,283,470 B2
(45) Date of Patent: Oct. 9, 2012

(54) METHOD FOR THE PREPARATION OF SOLIFENACIN AND INTERMEDIATE THEREOF

(75) Inventors: Vijayvitthal Thippannachar Mathad, Maharashtra (IN); Navnath Chintaman Niphade, Maharashtra (IN); Anil Chaturlal Mali, Maharashtra (IN); Kunal Madhav Jagtap, Maharashtra (IN); Bhushan Sudhakar Pandit, Maharashtra (IN); P. Raghvendra Kumar, Maharashtra (IN); Shashikant Baburao Landge, Nashik (IN)

(73) Assignee: Megafine Pharma(P) Ltd., Mumbai, Maharashtra (IN)

( * ) Notice: Subject to any disclaimer, the term of this patent is extended or adjusted under 35 U.S.C. 154(b) by 0 days.

(21) Appl. No.: 13/255,561

(22) PCT Filed: Aug. 31, 2009

(86) PCT No.: PCT/IN2009/000476
§ 371 (c)(1),
(2), (4) Date: Sep. 9, 2011

(87) PCT Pub. No.: WO2010/103529
PCT Pub. Date: Sep. 16, 2010

(65) Prior Publication Data
US 2011/0319621 A1  Dec. 29, 2011

(30) Foreign Application Priority Data
Mar. 9, 2009 (IN) .......................... 519/MUM/2009

(51) Int. Cl.
*C07D 453/04* (2006.01)
*A61K 31/44* (2006.01)

(52) U.S. Cl. ...................................... 546/134; 514/305

(58) Field of Classification Search ............ 546/124, 546/141
See application file for complete search history.

(56) References Cited

FOREIGN PATENT DOCUMENTS

| EP | 0801067 | 10/1997 |
| EP | 1757604 | 2/2007 |
| EP | 2088148 | 8/2009 |
| WO | WO-2005/075474 | 8/2005 |
| WO | WO-2008/120080 | 10/2008 |
| WO | WO-2010/103529 | 9/2010 |

OTHER PUBLICATIONS

Allegrini et. al., Casreact Abstract, "Process for the preparation of solifenacin", May 8, 2008.*
PCT Written Opinion in PCT/IN2009/000476, mailed May 28, 2010, 4 pgs.

* cited by examiner

*Primary Examiner* — Janet Andres
*Assistant Examiner* — Heidi Reese
(74) *Attorney, Agent, or Firm* — Diehl Servilla LLC

(57) ABSTRACT

A method for the preparation of solifenacin by reacting quinuclidin-3-ol and bis (aryl) carbonate to form (3R)-1-azabicyclo[2.2.2]oct-3-yl 4-aryl carbonate of formula (IVa); and treating (3R)-1-azabicyclo[2.2.2]oct-3-yl 4-aryl carbonate of formula (IVa) with (1S)-1-phenyl- 1,2,3,4-tetrahydroisoquinoline of formula (V) in an inert atmosphere to form a Solifenacin base, which is converted into its pharmaceutically acceptable salts. The invention also provides a compound, (3R)-1-azabicyclo[2.2.2]oct-3-yl 4-aryl carbonate of formula (IVa), which is used as an intermediate for the preparation of Solifenacin base and a process for the preparation thereof.

17 Claims, No Drawings

METHOD FOR THE PREPARATION OF SOLIFENACIN AND INTERMEDIATE THEREOF

CROSS-REFERENCE TO RELATED APPLICATIONS

This application is the National Stage entry of PCT/IN2009/000476, filed on Aug. 31, 2009, which claims priority to Indian Patent application number 519/MUM/2009, filed on Mar. 9, 2009, both of which are incorporated herein by reference in their entireties.

TECHNICAL FIELD

The present invention relates to a new method for the preparation of Solifenacin of formula (I);

Formula I and its pharmaceutically acceptable salts.

The present invention particurlay relates to enanatiometrically pure form of (S, R)-Solifenacin succinate.

The present invention also relates to (3R)-1-azabicyclo[2.2.2]oct-3-yl 4-aryl carbonate of formula (IVa);

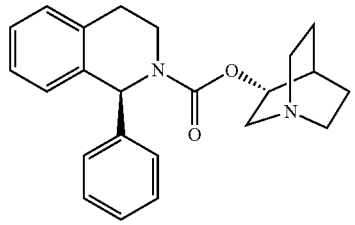

Formula-IVa which is used as an intermediate for the preparation of Solifenacin.

The present invention also relates to a process for the preparation of the compound of formula (IVa).

The present invention also particularly relates to (3R)-1-azabicyclo[2.2.2]oct-3-yl 4-nitrophenyl carbonate of formula (IV);

(IV)

which is used as an intermediate for the preparation of Solifenacin.

The present invention also relates to a process for the preparation of the compound of formula (IV).

BACKGROUND OF THE INVENTION

Solifenacin succinate is commercially marketed as pharmaceutically active substance indicated for the treatment of overactive bladder with symptoms of urinary incontinence, urgency and high urinary frequency. Solifenacin succinate is acting as a selective antagonist to the M (3)-receptor. The chemical name of the Solifenacin is (1S)-(3R)-1-azabicyclo[2.2.2]Oct-3-yl-3,4-dihydro-1-phenyl-2(1H)-isoquinoline carboxylate of formula (I);

Formula I

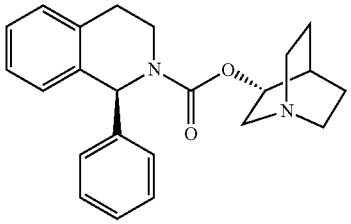

Solifenacin succinate is the international common denomination for butanedioic acid compounded with (1S)-(3R)-1-azabicyclo[2.2.2]oct-3-yl-3,4-dihydro-1-phenyl-2(1H)-isoquinolinecarboxylate (1:1), having an empirical formula of $C_{23}H_{26}N_2O_2 \cdot C_4H_6O_4$ and the structure is represented in formula VI given below;

Formula (VI)

Solifenacin and its pharmaceutically acceptable salts are first reported in U.S. Pat. No. 6,017,927 (927'), which disclosed two synthetic routes "Route-A and Route-B" for the preparation of (1RS,3'RS)-Solifenacin and (1S,3'RS)-Solifenacin as shown in Scheme-1:

Scheme 1: Reported synthetic schemes in US' 927

Route-A

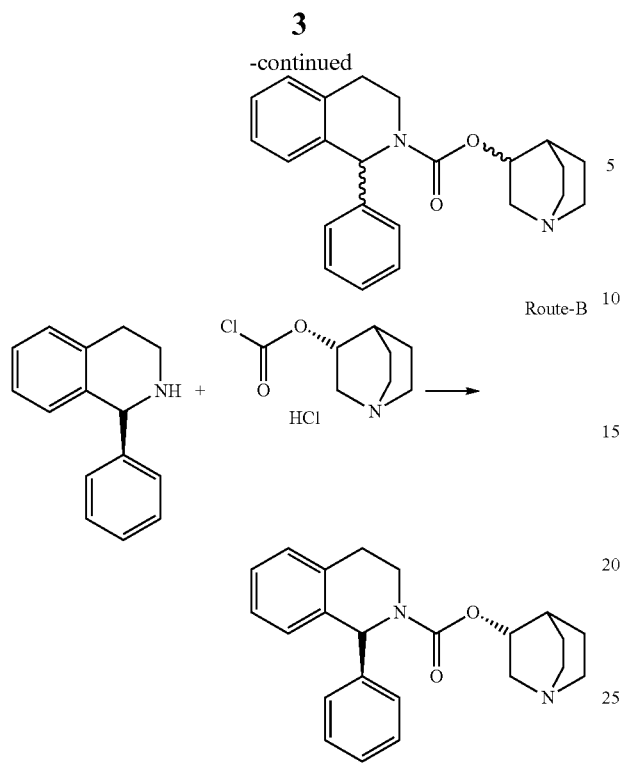

Both the routes have several drawbacks such as;

a) Use of hazardous and pyrophoric reagent, NaH, in the process which is very difficult to handle and thus makes the process unsafe to handle at industrial level. The use of strong agent NaH also leads to racemization of the products and thus suffers to provide enantiomerically pure Solifencin;

b) Use of ethylchloroformate to prepare ethylcarboxylate derivative in route A which is lachrymatory in nature;

c) Ethylcarboxylate derivative produces ethanol as a by-product during trans-esterification reaction in the subsequent reaction that interferes in nucleophilic attack against Solifenacin in the presence of a base and hence it is necessary to remove ethanol from the reaction mixture in the form of azeotrope with toluene or the like simultaneously while carrying out the reaction, so as to control the reaction;

d) Use of column chromatography for the purification of Solifenacin base, which makes the process industrially not feasible;

f) The reaction requires longer time for the completion and hence turn around time of the batch in production makes it less attractive.

International Patent Application No WO2005/075474 disclosed another synthetic route for the preparation of Solifenacin and Solifenacin succinate as shown in Scheme-2.

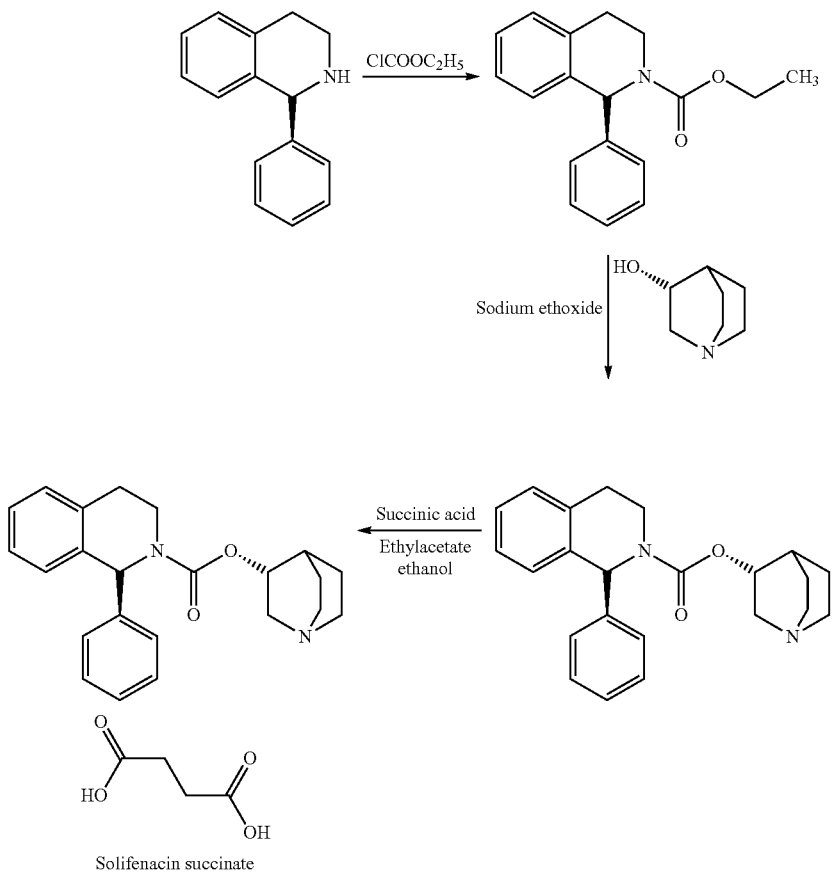

Solifenacin succinate

The above route does not overcome the problems associated with the process disclosed in 927' as the process described in this scheme also uses ethylchloroformate in the first step and produces ethanol as a by-product in the second step.

Yet another International Patent application no WO2005/105795A1 discloses an improved process for preparing Solifenacin as represented in Scheme-3, wherein leaving group (Lv) can be 1H-imidazole-1-yl, 2,5-dioxopyrrolidin-1-yloxy, 3-methyl-1H-imidazol-3-ium-1-yl or chloro and further condensation is carried out in the presence of sodium hydride as a base and a mixture of toluene and dimethylformamide or toluene alone as a reaction medium. The process described herein represents few draw backs such as, use of hazardous sodium hydride, use of chromatographic purifications, and use of moisture sensitive leaving groups (Lv) and hence handling of the reaction is difficult. Further the leaving groups used are expensive and thus making the process uneconomic.

Scheme 3

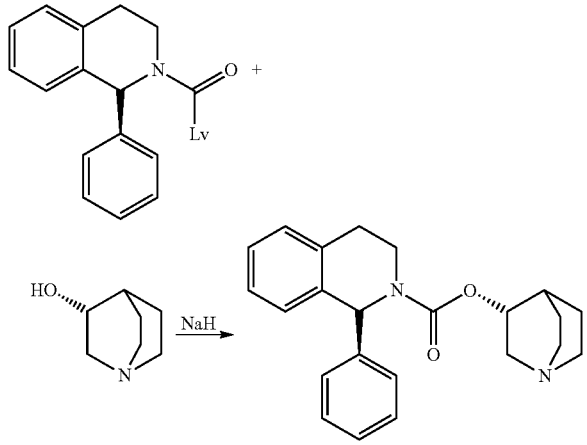

Hence, there is need of efficient process for producing Solifenacin and its succinate salt which is safe to handle, industrially feasible, and economically viable.

OBJECTS OF THE PRESENT INVENTION

An object of the present invention is to provide a new method for the preparation of Solifenacin and/or its salts, wherein the process is economical, simple, efficient, cost-effective and easy to carry out.

Another object of the invention is to provide the new method for the preparation of Solifenacin and/or its salts with high yields and substantially pure and free from impurities and thus making the process efficient.

Yet another object of the invention is to provide the new method for the preparation of Solifenacin and/or its salts in a single pot where in isolation of intermediates by filtrations are avoided to reduce exposure of the production executive to the chemicals and to reduce the turn around time of the total time cycle per batch.

Another object of the invention is to provide the new method for the preparation of Solifenacin and/or its salts which avoids hazardous and costly reagents or chemicals and involves simple work-up thus making the process simple and cost-effective.

Another object of the invention is to provide the enantimerically pure Solifenacin succinate, which is substantially free from other isomers and having chiral purity of 99.95% by the chiral HPLC method.

Yet another object of the invention is to provide (S,R)-Solifenacin succinate having chiral purity 99.95% and it is substantially free from other isomers, such as (R,R)-, (S,S)- and (R,S)-1-azabicyclo[2.2.2]Oct-3-yl-3,4-dihydro-1-phenyl-2(1H)-isoquinoline carboxylate.

Yet another object of the invention is to provide the new method for the preparation of Solifenacin and/or its salts in which nitro-phenol is a by-product which is easily separable and recoverable from the reaction mixture by vacuum distillation and giving monitory benefits to the process.

Yet another object of the invention is to provide a new compound having formula (IVa);

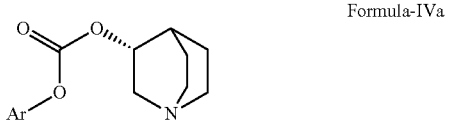

Formula-IVa

Wherein Ar: phenyl, substituted phenyl selected from p-nitro phenyl, 4-(trifluoro methyl)phenyl, 4-cyano phenyl, ethyl benzoate, benzoic acid, etc Yet another object of the invention is to provide a process for the preparation of the compound having formula (IVa).

Yet another object of the invention is to provide a new compound, (3R)-1-azabicyclo[2.2.2]oct-3-yl 4-nitrophenyl carbonate, of formula (IV), which is used as intermediate for the production of Solifenacin.

Yet another object of the invention is to provide a process for the preparation of (3R)-1-azabicyclo[2.2.2]oct-3-yl 4-nitrophenyl carbonate compound of formula (IV) which is used as an intermediate for the production of Solifenacin.

Yet another object of the invention is to provide a method for purifying the (R,S)-Solifenacin succinate to achieve chiral purity 99.95%, which also makes Solifenacin succinate substantially free from other isomers, such as (R,R)-, (S,S)- and (S,R)-1-azabicyclo[2.2.2]oct-3-yl-3,4-dihydro-1-phenyl-2 (1H)-isoquinoline carboxylate.

DETAILED DESCRIPTION OF THE INVENTION

The present invention provides a novel method for efficiently preparing Solifenacin and/or one of its pharmaceutically acceptable salts. According to the process of present invention, Solifenacin is obtained by using milder reaction conditions and without the need for laborious operations such as chromatographic purifications and drying or solvent distillations, and hazardous chemicals.

The process for making the compound (I) involves two chemical reactions. Accordingly, it will be described as a two-step process. While the steps are normally run separately, that is consecutively, the process may nonetheless be conveniently performed in a one pot arrangement as well, e.g. as a one pot process with out isolation of the intermediate product According to one of the embodiments of the invention, there is provided a new method for the preparation of (1S)-(3R)-1-azabicyclo[2.2.2]oct-3-yl-3,4-dihydro-1-phenyl-2 (1H)-isoquinolinecarboxylate, Solifenacin of formula (I);

Formula I

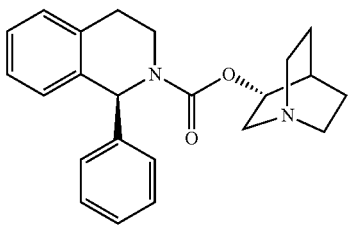

the method comprises;

a. reacting (R)-quinuclidin-3-ol of formula (II) and bis(aryl) carbonate of formula (IIIa) to form (3R)-1-azabicyclo[2.2.2]oct-3-yl 4-aryl carbonate of formula (IVa); and

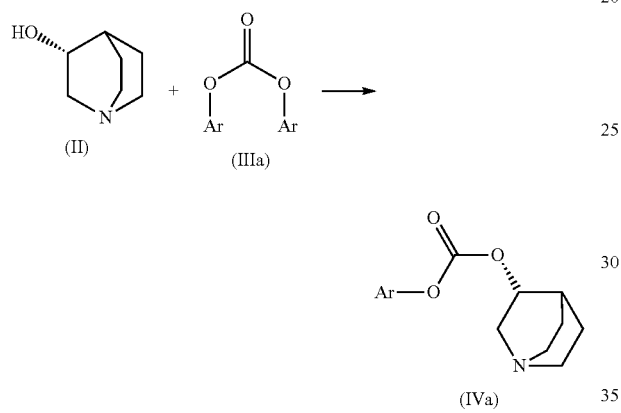

Wherein Ar: phenyl, substituted phenyl selected from p-nitro phenyl, 4-(trifluoro methyl)phenyl, 4-cyano phenyl, ethyl benzoate, benzoic acid, etc b. treating the reaction mixture comprising (3R)-1-azabicyclo[2.2.2]oct-3-yl-4-aryl carbonate of the formula (IVa) obtained from step (a) with (1S)-1-phenyl-1,2,3,4-tetrahydroisoquinoline of formula (v) to obtain (1S)-(3R)-1-azabicyclo[2.2.2]oct-3-yl-3,4-dihydro-1-phenyl-2(1H)-isoquinoline carboxylate (Solifenacin) of formula (I).

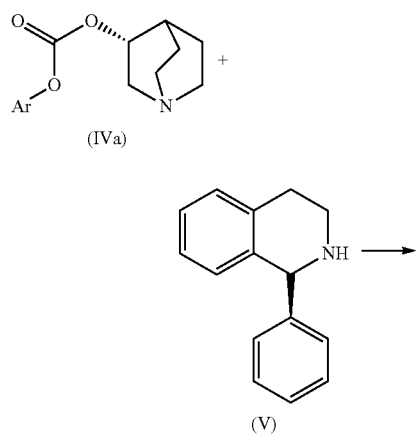

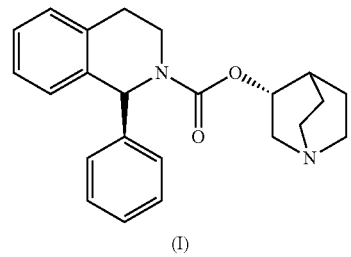

Wherein Ar: phenyl, substituted phenyl selected from p-nitro phenyl, 4-(trifluoro methyl)phenyl, 4-cyano phenyl, ethyl benzoate, benzoic acid, etc Step (a) of the above method comprises reacting (R)-quinuclidin-3-ol of formula (II) and bis(aryl)carbonate of formula (III) in an organic solvent and in an inert atmosphere at temperature of −40 to 100° C.

Bis(aryl)carbonate of formula (III) is selected from diphenyl carbonate, bis(p-nitrophenyl)carbonate, bis[4-(trifluoromethyl)phenyl]carbonate, bis(4-cyanophenyl)carbonate, diethyl 4,4'-[carbonylbis(oxy)]dibenzoate, 4,4'-[carbonylbis(oxy)]dibenzoic acid, etc. Preferably, bis(aryl)carbonate is bis(p-nitrophenyl)carbonate.

According to the invention, there is provided a new method for the preparation of (1S)-(3R)-1-azabicyclo[2.2.2]oct-3-yl-3,4-dihydro-1-phenyl-2(1H)-isoquinolinecarboxylate, Solifenacin of formula (I);

Formula I

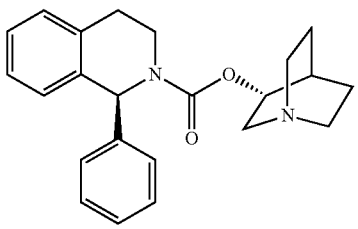

the method comprises;

a. reacting (R)-quinuclidin-3-ol of formula (II) and bis(p-nitrophenyl)carbonate of formula (III) to form (3R)-1-azabicyclo[2.2.2]oct-3-yl-4-nitrophenyl carbonate of formula (IV); and

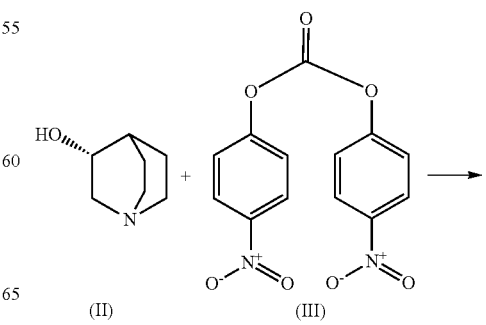

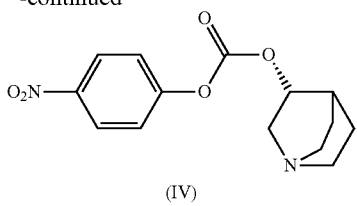

b. treating the reaction mixture comprising (3R)-1-azabicyclo[2.2.2]oct-3-yl-4-nitrophenyl carbonate of the formula (IV) obtained from step (a) with (1S)-1-phenyl-1,2,3,4-tetrahydroisoquinoline of formula (V) to obtain (1S)-(3R)-1-azabicyclo[2.2.2]oct-3-yl-3,4-dihydro-1-phenyl-2(1H)-isoquinolinecarboxylate (Solifenacin) of formula (I).

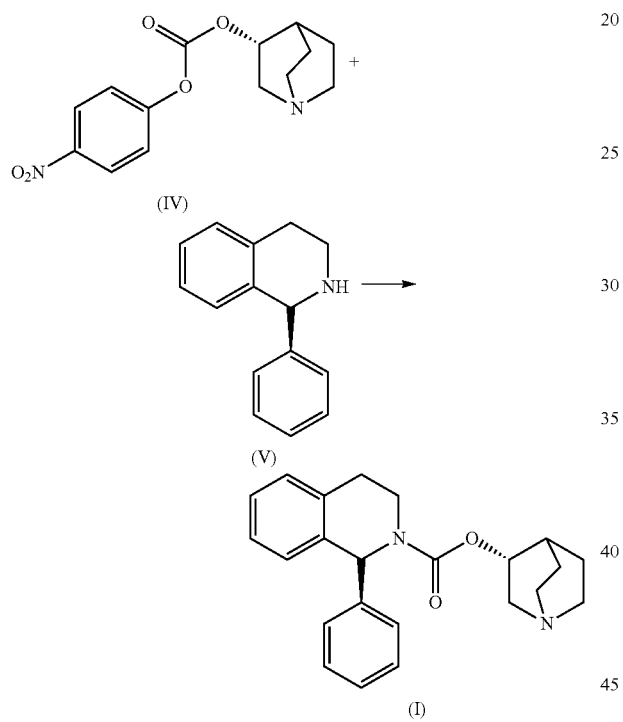

Step (a) of the above method comprises reacting (R)-quinuclidin-3-ol formula (II) and bis(p-nitrophenyl) carbonate of formula (III) in an organic solvent and in an inert atmosphere at temperature of −40 to 100° C.

Step (a) of the above-mentioned processes optionally carried out in the presence of suitable base.

Preferably, step (a) of the above-mentioned processes is carried out at temperature of 0 to 30° C., more preferably, 25 to 30° C.

The organic solvents used in the above reaction of step (a) is selected from the group consisting of a C1-C10 ether, a C5-C8 cyclic ether, C2-10 aliphatic ester, C2-C8 aliphatic amides, sulfoxide, C5-C8 cyclic amines, C5-C10 aliphatic amines, C1-C8 chlorinated hydrocarbon, and mixtures of thereof. Preferably, the solvent is selected from dimethylformamide, N-methylpyrolidone, N,N-dimethylacetamide, dimethyl sulfoxide, chlorinated hydrocarbon, pyridine, and mixtures thereof. More preferably, the solvent is dimethylformamide.

The reaction time of step (a) is invariably depends on the temperature condition used to carry out the step (a). The reaction time increases with decrease in temperature.

The course of the reaction is monitored by a suitable analytical method, for instance by HPLC and/or by TLC, and the second step of the reaction process does not start until the first reaction step is essentially completed, i.e. more than 95%, preferably more than 98% of the starting material has been converted/consumed which requires around 2-3 hours at 25-30° C.

The above mentioned step (b) comprises treating the reaction mixture comprising (3R)-1-azabicyclo[2.2.2]oct-3-yl 4-aryl carbonate of formula (IVa) of step (a) with (1S)-1-phenyl-1,2,3,4-tetrahydroisoquinoline of formula (V) in an organic solvent and in an inert atmosphere at temperature of −20 to 50° C. to obtain (1S)-(3R)-1-azabicyclo[2.2.2]oct-3-yl-3,4-dihydro-1-phenyl-2(1H)-isoquinolinecarboxylate (Solifenacin) of formula (I).

The above mentioned step (b) comprises treating the reaction mixture comprising (3R)-1-azabicyclo[2.2.2]oct-3-yl 4-nitrophenyl carbonate of formula (IV) of step (a) with (1S)-1-phenyl-1,2,3,4-tetrahydroisoquinoline of formula (V) in an organic solvent and in an inert atmosphere at temperature of −20 to 50° C. to obtain (1S)-(3R)-1-azabicyclo[2.2.2]oct-3-yl-3,4-dihydro-1-phenyl-2(1H)-isoquinolinecarboxylate (Solifenacin) of formula (I).

The process of step (b) typically comprise adding (1S)-1-phenyl-1,2,3,4-tetrahydroisoquinoline of formula (V) to the reaction mixture of step (a) in portion wise or at once, as such or dissolved in the organic solvent. Step (b) proceeds while stirring the reaction mixture.

Step (b) is carried out preferably at temperature of 0 to 30° C.; most preferably 25 to 30° C.

Step (b) of the method is monitored by a suitable analytical process, for instances by HPLC and/or by TLC.

The above mentioned method further/optionally comprises
  a. Isolating (3R)-1-azabicyclo[2.2.2]oct-3-yl-4-aryl carbonate of formula (IVa) from the reaction mixture obtained in step (a) of the above-mentioned process; and
  b. Reacting (3R)-1-azabicyclo[2.2.2]oct-3-yl 4-aryl carbonate of formula (IVa) with (1S)-1-phenyl-1,2,3,4-tetrahydroisoquinoline of formula (V) to form a (1S)-(3R)-1-azabicyclo[2.2.2]oct-3-yl-3,4-dihydro-1-phenyl-2(1H)-isoquinolinecarboxylate of formula (I).

(3R)-1-azabicyclo[2.2.2]oct-3-yl-4-aryl carbonate of formula (IVa) is isolated from the reaction mixture obtained in step (a) by
  1. separating out the aryl alcohol from the reaction mixture obtained from step (a) by distilling out the organic solvent under vacuum from the reaction mass of step (a) to get residue, adding water to the residue, adjusting the pH of the resultant mixture to 1 to 2 using an acid, preferably hydrochloric acid; extracting the reaction mass with a water immiscible organic solvent to separate out aryl alcohol;
  2. isolating the compound of formula (IVa) by extracting the aqueous layer obtained from step (1) with a water immiscible organic solvent to separate the compound of formula (IVa), diluting the organic layer comprising the compound of formula (IVa) with water, adjusting pH of the resulting mixture to 9 to 13, preferably between 9 to 10 using base, separating the organic layer, washed with water, and then concentrated to yield compound of Formula (IVa) as a syrup.

Bis(aryl)carbonate, compound (IIIa) is selected from diphenyl carbonate, bis(p-nitrophenyl)carbonate, bis[4-(trifluoromethyl)phenyl]carbonate, bis(4-cyanophenyl)carbonate, diethyl 4,4'-[carbonylbis(oxy)]dibenzoate, 4,4'-[carbonylbis(oxy)]dibenzoic acid, etc.

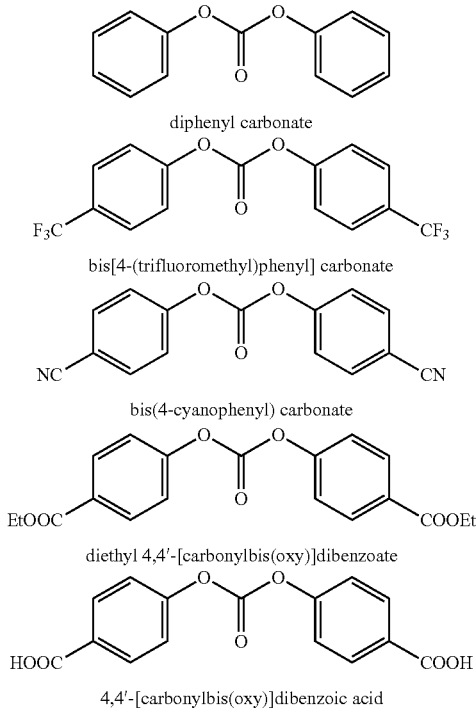

diphenyl carbonate bis[4-(trifluoromethyl)phenyl] carbonate bis(4-cyanophenyl) carbonate diethyl 4,4'-[carbonylbis(oxy)]dibenzoate 4,4'-[carbonylbis(oxy)]dibenzoic acid Preferably, bis(aryl)carbonate is bis(p-nitrophenyl)carbonate.

Use of Bis(aryl)carbonate, compound (IIIa) such as diphenyl carbonate, bis(p-nitrophenyl)carbonate, bis[4-(trifluoromethyl)phenyl]carbonate, bis(4-cyanophenyl)carbonate, diethyl 4,4'-[carbonylbis(oxy)]dibenzoate, 4,4'-[carbonylbis(oxy)]dibenzoic acid, etc gives Compound (IVa) such as (3R)-1-azabicyclo[2.2.2]oct-3-yl 4-phenyl carbonate, (3R)-1-azabicyclo[2.2.2]oct-3-yl 4-nitro phenyl carbonate, (3R)-1-azabicyclo[2.2.2]oct-3-yl 4-4-(trifluoromethyl)phenyl carbonate, (3R)-1-azabicyclo[2.2.2]oct-3-yl 4-cyano phenyl carbonate, (3R)-1-azabicyclo[2.2.2]oct-3-yl 4-ethyl benzoate carbonate, (3R)-1-azabicyclo[2.2.2]oct-3-yl 4-benzoic acid carbonate, etc.

When Compound (IIIa) is bis(p-nitrophenyl)carbonate of formula (III) then step (a) gives (3R)-1-azabicyclo[2.2.2]oct-3-yl-4-nitrophenyl carbonate of the formula (IV); then Step (b) releases p-nitro phenol as aryl alcohol.

Similarly

When Compound (IIIa) is bis(phenyl)carbonate of formula (III) then step (a) gives (3R)-1-azabicyclo[2.2.2]oct-3-yl-4-phenyl carbonate of the formula (IV); then Step (b) releases phenol as aryl alcohol.

When Compound (IIIa) is bis[4-(trifluoromethyl)phenyl] carbonate of formula (III) then step (a) gives (3R)-1-azabicyclo[2.2.2]oct-3-yl-4-(4-(trifluoromethyl)phenyl carbonate of the formula (IV); then Step (b) releases p-trifluoromethyl phenol as aryl alcohol.

When Compound (IIIa) is bis(4-cyanophenyl)carbonate of formula (III) then step (a) gives (3R)-1-azabicyclo[2.2.2]oct-3-yl-4-cyano phenyl carbonate of the formula (IV); then Step (b) releases p-cyanophenol as aryl alcohol.

When Compound (IIIa) is diethyl 4,4'-[carbonylbis(oxy)] dibenzoate of formula (III) then step (a) gives (3R)-1-azabicyclo[2.2.2]oct-3-yl-4-(ethyl benzoate) carbonate of the formula (IV); then Step (b) releases p-hydroxy ethyl benzoate as aryl alcohol.

When Compound (IIIa) is 4,4'-[carbonylbis(oxy)]dibenzoic acid of formula (III) then step (a) gives (3R)-1-azabicyclo[2.2.2]oct-3-yl-4-(carboxy phenyl)carbonate of the formula (IV); then Step (b) releases p-hydroxy benzoic acid as aryl alcohol.

The above mentioned method further/optionally comprises
a. Isolating (3R)-1-azabicyclo[2.2.2]oct-3-yl-4-nitro phenyl carbonate of formula (IV) from the reaction mixture obtained in step (a) of the above-mentioned process; and
b. Reacting (3R)-1-azabicyclo[2.2.2]oct-3-yl 4-nitrophenyl carbonate of formula (IV) with (1S)-1-phenyl-1,2,3,4-tetrahydroisoquinoline of formula (V) to form a (1S)-(3R)-1-azabicyclo[2.2.2]oct-3-yl-3,4-dihydro-1-phenyl-2(1H)-isoquinolinecarboxylate of formula (I).

The above mentioned method further/optionally comprises:

Isolating (3R)-1-azabicyclo[2.2.2]oct-3-yl-4-nitrophenyl carbonate of formula (IV) from the reaction mixture obtained in step (a) by
1. separating out the nitro-phenol from the reaction mixture obtained from step (a) by distilling out the organic solvent under vacuum from the reaction mass of step (a) to get residue, adding water to the residue, adjusting the pH of the resultant mixture to 1 to 2 using an acid, preferably hydrochloric acid; extracting the reaction mass with a water immiscible organic solvent to separate out nitro-phenol;
2. isolating the compound of formula (IV) by extracting the aqueous layer obtained from step (1) with a water immiscible organic solvent to separate the compound of formula (IV), diluting the organic layer comprising the compound of formula (IV) with water, adjusting pH of the resulting mixture to 9 to 13, preferably between 9 to 10 using base, separating the organic layer, washed with water, and then concentrated to yield compound of Formula (IV) as a syrup.

The method of the invention further comprises isolation of (1S)-(3R)-1-azabicyclo[2.2.2]oct-3-yl-3,4-dihydro-1-phenyl-2(1H)-isoquinolinecarboxylate (Solifenacin) of formula (I) by
1. Separating aryl alcohol such as phenol, p-nitro phenol, p-trifluoromethyl phenol, p-cyano phenol, p-hydroxy ethyl benzoate, p-hydroxy benzoic acid, etc from the reaction mass obtained from step (b);
by adding water to the reaction mass obtained from step (b) followed by adjusting pH to 1-2 by using acid, preferably hydrochloric acid, adding water immiscible organic solvent to the reaction mass followed by mixing the reaction mass, separating out the water immiscible organic layer comprising nitro-phenol and aqueous layer comprising hydrochloride salt of (3R)-3-[(1S)-1-phenyl-1,2,3,4-tetrahydro-2-isoquinolinyl carbonyloxy]-1-azabicyclo[2.2.2]octane of formula (I);
and
2. isolating (3R)-3-[(1S)-1-phenyl-1,2,3,4-tetrahydro-2-isoquinolinylcarbonyloxy]-1-azabicyclo[2.2.2]octane of the formula (I) by extracting the hydrochloride salt of compound of formula (I) in a water immiscible organic solvent from the aqueous layer obtained from the above mentioned step (a), adding water to the organic layer followed by adjusting the pH of the solution to 9 to 13 by adding base followed by separating aqueous layer and organic layer comprising (3R)-3-[(1S)-1-phenyl-1,2,3,4-tetrahydro-2-isoquinolinylcarbonyloxy]-1-azabicyclo[2.2.2] octane of formula (I); washing the organic layer with water and concentrating the organic layer to yield compound of the formula (I) as syrup/oil.

The method of the invention further comprises isolation of (1S)-(3R)-1-azabicyclo[2.2.2]oct-3-yl-3,4-dihydro-1-phenyl-2(1H)-isoquinolinecarboxylate (Solifenacin) of formula (I) by 1. Separating the by-product, aryl alcohol such as phenol, p-nitro phenol, p-trifluoromethyl phenol, p-cyano phenol, p-hydroxy ethyl benzoate, p-hydroxy benzoic acid, etc from the reaction mass obtained from step (b);
   by adding water to the reaction mass obtained from step (b) followed by adjusting the pH to 1-2 by using acid, preferably hydrochloric acid, adding water-immiscible organic solvent to the reaction mass followed by mixing the reaction mass, separating out the water-immiscible organic layer comprising nitro-phenol and aqueous layer comprising hydrochloride salt of (1S)-(3R)-1-azabicyclo[2.2.2]oct-3-yl-3,4-dihydro-1-phenyl-2 (1H)-isoquinolinecarboxylate of formula (I); and
2. isolating (1S)-(3R)-1-azabicyclo[2.2.2]oct-3-yl-3,4-dihydro-1-phenyl-2(1H)-isoquinoline carboxylate of the formula (I) by extracting the hydrochloride salt of compound of formula (I) in a water-immiscible organic solvent from the aqueous layer obtained from the above mentioned step (1), distilling off the solvent from the organic layer to obtain a residue, dissolving the residue in a mixture of water and a water-immiscible organic solvent followed by adjusting the pH of the solution to 9 to 13 by adding base followed by separating aqueous layer and organic layer comprising (1S)-(3R)-1-azabicyclo[2.2.2]oct-3-yl-3,4-dihydro-1-phenyl-2(1H)-isoquinolinecarboxylate of formula (I); washing the organic layer with water followed with solution of 0.5% of sodium hydroxide and concentrating the organic layer to yield compound of the formula (I) as syrup/oil.

The water immiscible organic solvent used in the separation of p-nitro phenol is selected to essentially separate the by-product nitro phenol from the reaction mixture. The organic solvent is selected from esters such as ethyl acetate, isopropyl acetate, isobutyl acetate and the like; ethers such as diethyl ether, diisopropylether, methyl-tert-butylether and the like; hydrocarbons such as toluene, xylene, heptane, pentane, cyclohexane and the like; and mixtures of thereof; preferably, the solvent is selected from ethers, more preferably, diisopropylether.

The above mentioned method further comprises isolation of nitro phenol as potential by-product by distilling out ether from the ether layer comprising nitro-phenol obtained in the above mentioned step (1).

The organic solvent used for the extracting the compound of formula (IV) is selected from, esters such as ethyl acetate, isopropyl acetate, isobutyl acetate and the like; ethers such as diethyl ether, diisopropylether, methyl-tert-butylether and the like; hydrocarbons such as toluene, xylene, heptane, pentane, cyclohexane and the like; chlorinated hydrocarbons such as dichloromethane, dichloroethane, chloroform, and the like, and mixtures of thereof.

The water immiscible organic solvent used for the extraction of Solifenacin hydrochloride is selected from, esters such as ethyl acetate, isopropyl acetate, isobutyl acetate and the like; ethers such as diethyl ether, diisopropylether, methyl-tert-butylether and the like; hydrocarbons such as toluene, xylene, heptane, pentane, cyclohexane and the like; chlorinated hydrocarbons such as dichloromethane, dichlorethane, chloroform, and the like, and mixtures of thereof; preferably, said solvent is selected from hydrocarbons, or chlorinated hydrocarbons; more preferably dichloromethane.

Preferably, the pH of the solution of step (2) is adjusted to 9 to 13. The pH adjustment in step (2) is carried out using base such as sodium hydroxide, potassium hydroxide, sodium carbonate, potassium carbonate, ammonium hydroxide and the like, preferably ammonium hydroxide.

The water immiscible organic solvent used for the extraction of Solifenacin base in step (2) while adjusting the pH is selected from, esters such as ethyl acetate, isopropyl acetate, isobutyl acetate and the like; ethers such as diethyl ether, diisopropylether, methyl-tert-butylether and the like; hydrocarbons such as toluene, xylene, heptane, pentane, cyclohexane and the like; chlorinated hydrocarbons such as dichloromethane, dichlorethane, chloroform, and the like, and mixtures of thereof; preferably, said solvent is selected from hydrocarbons; more preferably toluene.

The above mentioned method further comprises converting a Solifenacin base of the compound of formula (I) into its pharmaceutically acceptable salts. The compound of the formula (I) is isolated as oil/syrup which is dissolved in an organic solvent and treated with the suitable acid selected from organic acids or inorganic acids to get salt. The acid can be hydrobromic acid or succinic acid; preferably succinic acid.

According to the present invention, the method for producing the Solifenacin Succinate of formula (VI) comprises; dissolving the Solifenacin of formula (I) obtained in step (b) in a organic solvent and then treating the same with succininc acid either in solid form or in dissolved form using the organic solvent, the reaction mixture is heated to dissolve the contents, cooled and the product precipitated is isolated by filtration which is further dried under vacuum to yield the Solifenacin Succinate of formula (VI).

The organic solvent for the preparation of pharmaceutically acceptable salt is selected from ketones such as acetone, ethylmethylketone, methylisobutylketone; esters such as ethyl acetate, isopropyl acetate, isobutyl acetate and the like; alcohols such as methanol, ethanol, isopropanol, butanol, tert-butanol and like; ethers such as diethylether, diisopropylether, methyl-tert-butylether and the like; hydrocarbons such as toluene, xylene, heptane, pentatne, cyclohexane and the like; and mixtures of thereof. Preferably, said solvent is selected from alcohols or ketones or mixtures thereof, more preferably said solvent is toluene or ethanol or acetone or mixtures thereof.

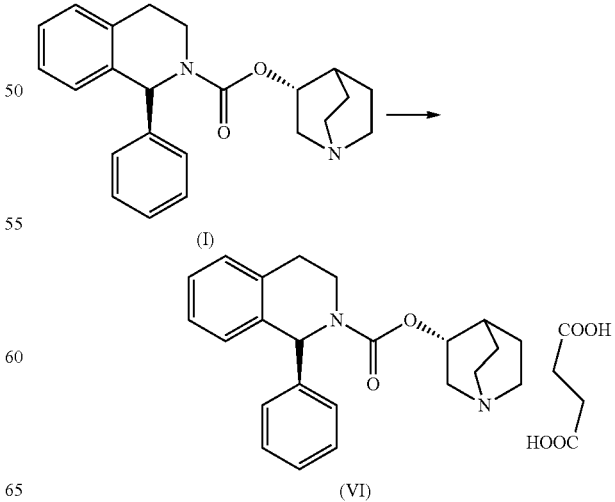

According to the invention, Solifencin base of formula (I) and Solifenaicn succinate salt of formula (VI) is having yield of 81% and 76.1% respectively and purity of at least of 98.0% and at least of 99.93% respectively by HPLC (High performance liquid chromatography).

Optionally Solifenacin Succinate obtained above can be purified by braking and making the salt; the said process comprises; dissolving the salt in water and a water-immiscible organic solvent followed by adjusting the pH of the solution to 9 to 13 by adding base followed by separating organic layer comprising (1S)-(3R)-1-azabicyclo[2.2.2]oct-3-yl-3,4-dihydro-1-phenyl-2(1H)-isoquinolinecarboxylate of formula (I); washing the organic layer with water and concentrating the organic layer to yield compound of the formula (I) as syrup/oil, which was further converted to solifenacin succinate salt of Formula VI as described above.pppppppp The water-immiscible organic solvent used for purification of Solifenacin succinate is selected from esters such as ethyl acetate, isopropyl acetate, isobutyl acetate and the like; ethers such as diethyl ether, diisopropylether, methyl-tert-butylether and the like; hydrocarbons such as toluene; xylene, heptane, pentane, cyclohexane and the like; chlorinated hydrocarbons such as dichloromethane, dichlorethane, chloroform, and the like, and mixtures of thereof; preferably, said solvent is selected from hydrocarbons; more preferably toluene.

The chiral purity of Solifenacin succinate salt of the formula (VI) is at least 99.95% respectively by HPLC using chiral column.

According to the invention, estimation of chiral purity is achieved by chromatographic separation which is carried out by using a Chiralpak-IC, 5μ, 250×4.6 mm I.D column at 30° C. The mobile phase is prepared by mixing 600 volumes of n-hexane, 150 volumes of ethanol, 250 volumes of isopropyl alcohol and 1 volumes of diethylamine. The chromatograph is equipped with a 220 nm detector and the flow rate is 1.0 ml per minute. 20 μl of the test samples are prepared by dissolving the appropriate amount of sample to obtain 1 mg per ml of a mixture of n-hexane/ethanol/isopropyl alcohol/diethylamine (60:15:25:0.1 v/v/v/v).

According to the invention, estimation of chromatographic purity is achieved by chromatographic separation which is carried out by using a ZORBAX SB-CN, 5μ,250×4.6 mm I.D column at 35° C. The mobile phase A is a buffer which is prepared from 3.4 gm of potassium dihydrogen orththophosphate and dissolving it in 1000 ml of water and adjusting to pH=3.5 with 5% v/v orthophosphoric acid. This mobile phase is mixed and filtered through 0.45 μm nylon filter under vacuum; the mobile phase B is a mixture of Acetonitrile: Methanol:Water (40:40:20 v/v/v)

The gradient profile of chromatographic method is programmed as follows:

Initial 0-8 min, isocratic 40% mobile phase B, 8-10 min linear gradient to 50% mobile phase B, again 10-30 min. linear gradient to 90% mobile phase B, 30-50 min. isocratic 90% mobile phase B, 50-53 min. linear gradient to 40% mobile phase B and 53-60 min. equilibration to 40% mobile phase B. The chromatograph is equipped with a 220 nm detector and the flow rate is 1.0 ml per minute. 20 μl of the test samples are prepared by dissolving the appropriate amount of sample to obtain 2 mg per ml of a mixture of mobile phase A/mobile phase B (1:1).

The process of the present invention provides the Solifenaicin Succinate in highly pure form and substantially free from potential impurities.

According to the invention there is provided (S,R)-Solifenacin succinate having at least 99.95% of chiral purity which also makes Solifenacin Succinate substantially free from other isomers of (R,R)-, (S,S)- and (R,S)-1-azabicyclo[2.2.2] Oct-3-yl-3,4-dihydro-1-phenyl-2(1H)-isoquinoline carboxylate. This is possible to achieve as the process is carried out in absence of strong base and high temperature followed by efficient work up and purification process.

Quinuclidin-3-ol of formula (II) and 1-phenyl-1,2,3,4-tetrahydroisoquinoline of formula (V) used in the above mentioned method may be either (R)-enantiomer, (S)-enantiomer or racemate depend upon the isomer of Solifenacin need to be prepared and are shown below.

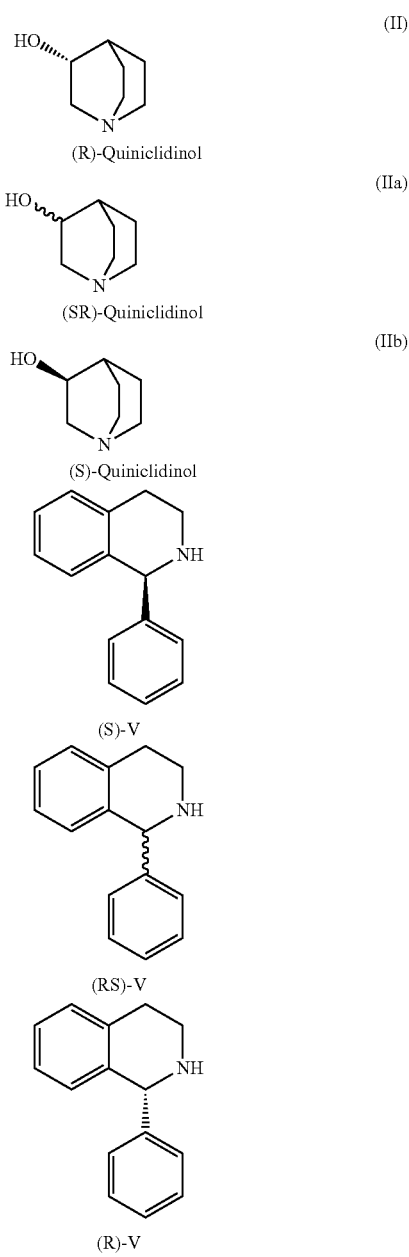

Achieving the desired stereochemistry of the Solifenacin depends upon the selection of suitable isomers of starting materials such as quinuclidin-3-ol of formula (II) and 1-phenyl-1,2,3,4-tetrahydroisoquinoline of formula (V). (3R)-quinuclidin-3-ol of formula (II) and (1S)-1-phenyl-1,2,3,4-tetrahydroisoquinoline of formula (V) is used to obtain (1S,3R)-Solifenacin that is used for pharmaceutical purpose. The use of other isomers will lead to the formation of corresponding enantiomers of Solifenacin such as, (1R,3S)-1-azabicyclo[2.2.2]Oct-3-yl-3,4-dihydro-1-phenyl-2(1H)-isoquinoline carboxylate of Formula (Ia), (1R,3R)-1-azabicyclo[2.2.2]Oct-3-yl-3,4-dihydro-1-phenyl-2(1H)-isoquinoline carboxylate of formula (Ib), and (1S,3S)-1-azabicyclo[2.2.2]Oct-3-yl-3,4-dihydro-1-phenyl-2(1H)-isoquinoline carboxylate of Formula (Ic),

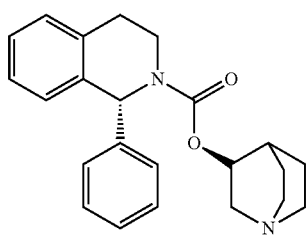
(Ia)

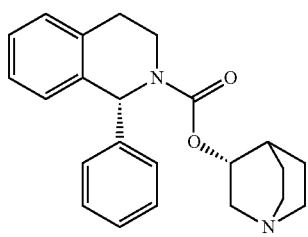
(Ib)

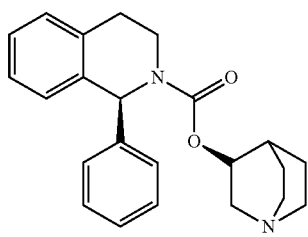
(Ic)

According to the invention, Solifenacin or its pharmaceutically acceptable salt obtained is highly pure and having purity of at least of 99.95% by HPLC. Further Solifenacin or its pharmaceutically acceptable salt obtained is substantially free from enantiomeric impurities.

According to the invention there is provided a compound having formula (IVa);

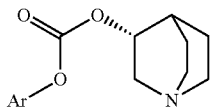
Formula-IVa

Wherein Ar: phenyl, substituted phenyl selected from p-nitro phenyl, 4-(trifluoro methyl)phenyl, 4-cyano phenyl, ethyl benzoate, benzoic acid, etc as an intermediate of Solifenacin.

The compound (IVa) is selected from (3R)-1-azabicyclo[2.2.2]oct-3-yl 4-phenyl carbonate, (3R)-1-azabicyclo[2.2.2]oct-3-yl 4-nitro phenyl carbonate, (3R)-1-azabicyclo[2.2.2]oct-3-yl 4-4-(trifluoromethyl)phenyl carbonate, (3R)-1-azabicyclo[2.2.2]oct-3-yl 4-cyano phenyl carbonate, (3R)-1-azabicyclo[2.2.2]oct-3-yl 4-ethyl benzoate carbonate, (3R)-1-azabicyclo[2.2.2]oct-3-yl 4-benzoic acid carbonate, etc.

This compound is preferably (3R)-1-azabicyclo[2.2.2]oct-3-yl-4-nitro phenyl carbonate.

A process for the preparation of compound of formula (IVa);

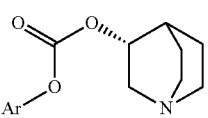
Formula-IVa

Wherein Ar: phenyl, substituted phenyl selected from p-nitro phenyl, 4-(trifluoro methyl)phenyl, 4-cyano phenyl, ethyl benzoate, benzoic acid, etc
the process comprising:
a. reacting (R)-quinuclidin-3-ol formula (II);

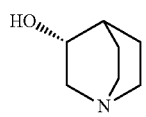
Formula-IVa with bis(aryl)carbonate of formula (IIIa);

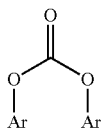
Formula-IIIa

Wherein Ar: phenyl, substituted phenyl selected from p-nitro phenyl, 4-(trifluoro methyl)phenyl, 4-cyano phenyl, ethyl benzoate, benzoic acid, etc
to form the compound of formula (IVa) and
b. isolating the compound of the formula (N) from the reaction mass of step (a).

Preferably (R)-quinuclidin-3-ol formula (II), is treated with bis(aryl)carbonate of formula (Ma) in an organic solvent and in an inert atmosphere at temperature of −40 to 100° C.

The step (a) may also be carried out in the presence of suitable base.

Preferably, step (a) is carried out temperature of 0 to 30° C., more preferably, 25 to 30° C.

The organic solvents used in the above reaction of step (a) is selected from the group consisting of a C1-C10 ether, a C5-C8 cyclic ether, C2-10 aliphatic ester, C2-C8 aliphatic amides, sulfoxide, C5-C8 cyclic amines, C5-C10 aliphatic amines, C1-C8 chlorinated hydrocarbon, and mixtures of thereof; preferably, the solvent is selected from dimethylformamide, N-methylpyrolidone, N,N-dimethylacetamide, dimethyl sulfoxide, chlorinated hydrocarbon, pyridine, and mixtures thereof; more preferably, the solvent is dimethylformamide or dichloromethane or pyridine; most preferably the solvent is dichloromethane.

The reaction time of step (a) is inversely proportional to the temperature condition used to carry out step (a). The reaction time increases with decrease in temperature.

Step (a) of the reaction is monitored by a suitable analytical method, for instance by HPLC and/or by TLC and is allowed to complete the reaction more than 95%, preferably more than 98% which requires around 2-3 hours at 25-30° C.

When Compound (IIIa) is bis(p-nitrophenyl)carbonate of formula (III) then step (a) gives (3R)-1-azabicyclo[2.2.2]oct-3-yl-4-nitrophenyl carbonate of the formula (IV); then releases p-nitro phenol as aryl alcohol.

Similarly

When Compound (Ma) is bis(phenyl)carbonate of formula (III) then step (a) gives (3R)-1-azabicyclo[2.2.2]oct-3-yl-4-phenyl carbonate of the formula (IV); then releases phenol as aryl alcohol. When Compound (IIIa) is bis[4-(trifluoromethyl)phenyl]carbonate of formula (III) then step (a) gives (3R)-1-azabicyclo[2.2.2]oct-3-yl-4-(4-(trifluoromethyl)phenyl carbonate of the formula (IV); then releases p-trifluoromethyl phenol as aryl alcohol.

When Compound (IIIa) is bis(4-cyanophenyl)carbonate of formula (III) then step (a) gives (3R)-1-azabicyclo[2.2.2]oct-3-yl-4-cyano phenyl carbonate of the formula (IV); then releases p-cyanophenol as aryl alcohol.

When Compound (IIIa) is diethyl 4,4'-[carbonylbis(oxy)] dibenzoate of formula (III) then step (a) gives (3R)-1-azabicyclo[2.2.2]oct-3-yl-4-(ethyl benzoate) carbonate of the formula (IV); then releases p-hydroxy ethyl benzoate as aryl alcohol.

When Compound (IIIa) is 4,4'-[carbonylbis(oxy)]dibenzoic acid of formula (III) then step (a) gives (3R)-1-azabicyclo[2.2.2]oct-3-yl-4-(carboxy phenyl)carbonate of the formula (IV); then releases p-hydroxy benzoic acid as aryl alcohol.

According to the invention, there is provided a new compound (3R)-1-azabicyclo[2.2.2]oct-3-yl 4-nitrophenyl carbonate of formula (IV);

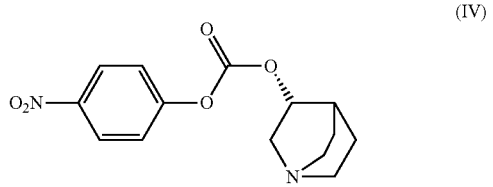

as an intermediate of Solifenacin.

According to the invention, there is provided a process for the preparation of new compound, (3R)-1-azabicyclo[2.2.2]oct-3-yl 4-nitrophenyl carbonate of formula (IV);

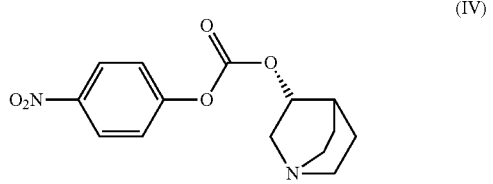

as an intermediate of Solifenacin,
  the process comprises;
  a reacting (R)-quinuclidin-3-ol of formula (II) and bis(p-nitro phenyl)carbonate of formula (III) to form (3R)-1-azabicyclo[2.2.2]oct-3-yl-4-nitrophenyl carbonate of formula (IV); and

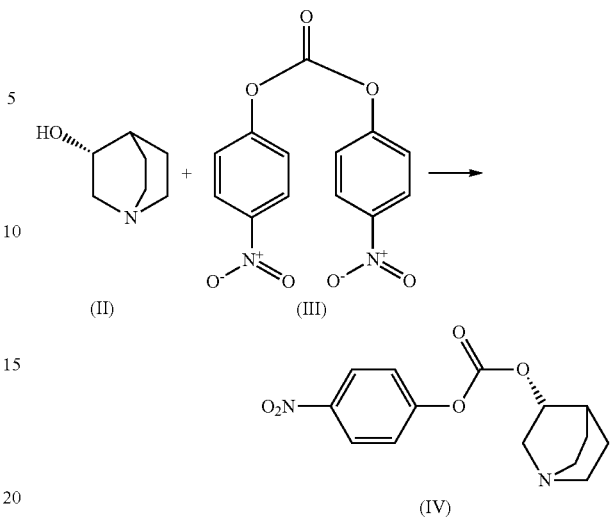

b isolating the compound of the formula (IV) from the reaction mass of step (a).

The step (a) comprises reacting (R)-quinuclidin-3-ol of formula (II) and bis(p-nitrophenyl)carbonate of formula (III) in an organic solvent and in an inert atmosphere at temperature of −40 to 100° C.

The step (a) may also be carried out in the presence of suitable base.

Preferably, step (a) is carried out temperature of 0 to 30° C., more preferably, 25 to 30° C.

The organic solvents used in the above reaction of step (a) is selected from the group consisting of a C1-C10 ether, a C5-C8 cyclic ether, C2-10 aliphatic ester, C2-C8 aliphatic amides, sulfoxide, C5-C8 cyclic amines, C5-C10 aliphatic amines, C1-C8 chlorinated hydrocarbon, and mixtures of thereof; preferably, the solvent is selected from dimethylformamide, N-methylpyrolidone, N,N-dimethylacetamide, dimethyl sulfoxide, chlorinated hydrocarbon, pyridine, and mixtures thereof; more preferably, the solvent is dimethylformamide or dichloromethane or pyridine; most preferably the solvent is dichloromethane.

The reaction time of step (a) is inversely proportional to the temperature condition used to carry out step (a). The reaction time increases with decrease in temperature.

Step (a) of the reaction is monitored by a suitable analytical method, for instance by HPLC and/or by TLC and is allowed to complete the reaction more than 95%, preferably more than 98% which requires around 2-3 hours at 25-30° C.

The isolation of the compound of formula (IVa) in step (b) is carried out by 1. separating out the aryl alcohol from the reaction mixture obtained from step (a) by distilling out the organic solvent under vacuum from the reaction mass of step (a) to get residue, adding water to the residue, adjusting the pH of the resultant mixture to 1 to 2 using an acid, preferably hydrochloric acid; extracting the reaction mass with a water immiscible organic solvent to separate out nitro-phenol;

2. isolating the compound of formula (IVa) by extracting the aqueous layer obtained from step (1) with a water immiscible organic solvent to separate the compound of formula (IVa), diluting the organic layer comprising the compound of formula (IVa) with water, adjusting pH of the resulting mixture to 9 to 13, preferably between 9 to 10 using base, separating the organic layer, washing the organic layer with water, and then concentrated to yield compound of Formula (IVa) as a syrup.

When Compound (IIIa) is bis(p-nitrophenyl)carbonate then step (a) gives (3R)-1-azabicyclo[2.2.2]oct-3-yl-4-nitrophenyl carbonate of the formula (IVa); then releases p-nitro phenol as aryl alcohol.

Similarly

When Compound (IIIa) is bis(p-nitrophenyl)carbonate of formula (III) then step (a) gives (3R)-1-azabicyclo[2.2.2]oct-3-yl-4-nitrophenyl carbonate of the formula (IV); then Step b releases p-nitro phenol as aryl alcohol.

Similarly

When Compound (IIIa) is bis(phenyl)carbonate of formula (III) then step (a) gives (3R)-1-azabicyclo[2.2.2]oct-3-yl-4-phenyl carbonate of the formula (IV); then releases phenol as aryl alcohol. When Compound (IIIa) is bis[4-(trifluoromethyl)phenyl]carbonate of formula (III) then step (a) gives (3R)-1-azabicyclo[2.2.2]oct-3-yl-4-(4-(trifluoromethyl)phenyl carbonate of the formula (IV); then releases p-trifluoromethyl phenol as aryl alcohol.

When Compound (IIIa) is bis(4-cyanophenyl)carbonate of formula (III) then step (a) gives (3R)-1-azabicyclo[2.2.2]oct-3-yl-4-cyano phenyl carbonate of the formula (IV); then releases p-cyanophenol as aryl alcohol.

When Compound (IIIa) is diethyl 4,4'-[carbonylbis(oxy)] dibenzoate of formula (III) then step (a) gives (3R)-1-azabicyclo[2.2.2]oct-3-yl-4-(ethyl benzoate) carbonate of the formula (IV); then releases p-hydroxy ethyl benzoate as aryl alcohol.

When Compound (IIIa) is 4,4'-[carbonylbis(oxy)]dibenzoic acid of formula (III) then step (a) gives (3R)-1-azabicyclo[2.2.2]oct-3-yl-4-(carboxy phenyl)carbonate of the formula (IV); then releases p-hydroxy benzoic acid as aryl alcohol.

The isolation of the compound of formula (IV) in step (b) is carried out by
1. separating out the nitro-phenol from the reaction mixture obtained from step (a) by distilling out the organic solvent under vacuum from the reaction mass of step (a) to get residue, adding water to the residue, adjusting the pH of the resultant mixture to 1 to 2 using an acid, preferably hydrochloric acid; extracting the reaction mass with a water immiscible organic solvent to separate out nitro-phenol;
2. isolating the compound of formula (IV) by extracting the aqueous layer obtained from step (I) with a water immiscible organic solvent to separate the compound of formula (IV), diluting the organic layer comprising the compound of formula (IV) with water, adjusting pH of the resulting mixture to 9 to 13, preferably between 9 to 10 using base, separating the organic layer, washing the organic layer with water, and then concentrated to yield compound of Formula (IV) as a syrup.

The organic solvent used for the separation of aryl alcohol like phenol, p-nitro phenol, p-trifluoromethyl phenol, p-cyano phenol, p-hydroxy ethyl benzoate, p-hydroxy benzoic acid, etc is selected from esters such as ethyl acetate, isopropyl acetate, isobutyl acetate and the like; ethers such as diethyl ether, diisopropylether, methyl-tert-butylether and the like; hydrocarbons such as toluene, xylene, heptane, pentane, cyclohexane and the like; and mixtures of thereof; preferably, said solvent is selected from ethers such as diisopropylether.

The process further comprises distilling out the solvent from the ether layer comprising aryl alcohol such as phenol, p-nitro phenol, p-trifluoromethyl phenol, p-cyano phenol, p-hydroxy ethyl benzoate, p-hydroxy benzoic acid, etc obtained from step (a) to isolate corresponding aryl alcohol.

The organic solvent used for the extracting the compound of formula (IVa)/formula (IV) is selected from, esters such as ethyl acetate, isopropyl acetate, isobutyl acetate and the like; ethers such as diethyl ether, diisopropylether, methyl-tert-butylether and the like; hydrocarbons such as toluene, xylene, heptane, pentane, cyclohexane and the like; chlorinated hydrocarbons such as dichloromethane, dichlorethane, chloroform, and the like, and mixtures of thereof; preferably, said solvent is selected from chlorinated hydrocarbons such as dichloromethane.

The base used to adjust the pH is selected from sodium hydroxide, potassium hydroxide, sodium carbonate, potassium carbonate, ammonium hydroxide and the like, more preferably the base used for the pH adjustment is ammonium hydroxide.

The isolated intermediate (IVa) or compound of formula (IV) from step (a) is used for the preparation of solifenacin of formula (I).

Thus the new method of the invention provides the method for the preparation of Solifenacin and/or its salts by which yield of Solifenacin and its Succinate salt obtained is 81% and 76.1% respectively in less time without sacrificing purity of at least 99.7% and at least 99.95% respectively thus making the process efficient. At the same time, chiral purity of Solifencin succinate salt of the formula (VI) is achieved as at least 99.95% respectively. The new method eliminates column chromatography and reduces reaction time. Workup of the reaction is simple as compared to the prior art. This method also avoids hazardous and costly reagents. Thus the process is simple and cost-effective. The method of the invention provides nitro-phenol as a by-product which is easily separable from the reaction mixture by vacuum distillation and giving monitory benefits.

The following experimental example is illustrative of the invention but not imitative of the scope thereof.

EXAMPLE 1

Preparation of Solifenacin Succinate of Formula (VI)

To a stirred solution of (3R)-quinuclidin-3-ol (25 gm) in dimethylformamide (175 ml) was added bis-(4-dinitrophenyl)carbonate (83.83 gm) with stirring at 25-30° C. under nitrogen atmosphere. The reaction mass was stirred at 25-30° C. for 2-3, hours. Upon completion of this reaction by HPLC, (1S)-1-phenyl-1,2,3,4-tetrahydroisoquinoline (41.0 gm) was added to resultant brown colored reaction solution and further stirred at 25-30° C. for 3-4 hrs. After completion of the reaction (monitored by HPLC), the reaction solution was diluted with water (250 ml) and the pH of the solution was adjusted to 1-2 using concentrated hydrochloric acid. The resulting reaction solution was extracted with diisopropylether (300 ml×2) to separate the nitro-phenol.

The aqueous layer was then extracted with dichloromethane (300 ml) and dichloromethane layer was separated and diluted with 200 ml water. The pH of the biphasic mixture was adjusted to 9-10 with ammonium hydroxide and organic layer was separated, washed with water (200 ml×2), and concentrated under vacuum to yield 57.0 gm (79%) of compound I as a syrup having HPLC purity of 98.8% and Chiral purity of 99.9%: Compound (I) was further dissolved in acetone (400 ml) and contacted with succinic acid (18.58 gm) at 25-30° C. and stirred for 30 min. Precipitated solid was filtered, washed with acetone (57 ml), and dried under vacuum to yield 53.0 gm solifenacin succinate of formula (VI) as a white crystalline solid; HPLC purity 99.93%; Chiral purity: 99.98%;

The ether layer comprising nitro-phenol was subjected to vacuum distillation to recover diisopropylether and nitro-phenol.

EXAMPLE 2

Preparation of Solifenacin Succinate of Formula (VI)

To a stirred solution of (3R)-quinuclidin-3-ol (5 gm) in dry pyridine (30 ml) was added bis-(4-dinitrophenyl)carbonate (17.5 gm) with stirring at 25-30° C. under nitrogen atmosphere. The reaction mass was stirred at 25-30° C. for 2-3 hours. Upon completion of the reaction by HPLC, (1S)-1-phenyl-1,2,3,4-tetrahydroisoquinoline (7.5 gm) was added to resultant brown colored reaction solution and further stirred at 25-30° C. for 3-4 hrs. After completion of the reaction (monitored by HPLC), the reaction solution was diluted with water (100 ml) and the pH of the solution was adjusted to 1-2 using concentrated hydrochloric acid. The resulting reaction solution was extracted with diisopropylether (60 ml×2) to separate the nitro-phenol.

The aqueous layer was then extracted with dichloromethane (60 ml), and dichloromethane layer was separated and diluted with 40 ml of water. The pH of the biphasic mixture was adjusted to 9-10 with ammonium hydroxide and organic layer was separated, washed with water (40 ml×2), and concentrated under vacuum to yield 10.0 gm (70.8%) of solifenacin of formula (I) as a syrup having HPLC purity of 97.9% and Chiral purity of 99.96%: Compound (I) was further dissolved in acetone (70 ml) and contacted with succinic acid (3.25 gm) at 25-30° C. and stirred for 30 min. Precipitated solid was filtered, washed with acetone (10 ml), and dried under vacuum to yield 8.5.0 gm solifenacin succinate of formula (VI) as a white crystalline solid; HPLC purity 99.78%; Chiral purity: 99.96%;

EXAMPLE 3

Preparation of Solifenacin Succinate of Formula (VI)

(3R)-quinuclidin-3-ol (1.0 gm) of was dissolved in tetrahydrofuran (15 ml) and dry pyridine (1.0 ml) with stirring. Bis-(4-dinitrophenyl)carbonate (3.82 gm) was added to the above solution at 25-30° C. After completion of the reaction, (1S)-1-phenyl-1,2,3,4-tetrahydroisoquinoline (1.5 gm) was added to the resulting brown reaction solution and then stirred till completion of the reaction. Upon completion of the reaction, the reaction solution was diluted with water (20 ml) and the pH of the solution was adjusted to 1-2 using concentrated hydrochloric acid. The resulting solution was extracted with diisopropylether (12.0 ml×2) to separate the nitro-phenol.

The aqueous layer was separated and further extracted with dichloromethane (12 ml×2). The dichloromethane layer was diluted with water (8 ml) and pH of the resulting mixture was adjusted to 9-10 using ammonium hydroxide solution. The aqueous layer was separated from organic layer, washed with water (8 ml×2) and concentrated to yield 1.5 gm (53.5%) solifenacin of Formula (I) having HPLC purity 96.47%; chiral purity 99.10%; Compound (I) was dissolved in acetone (10.5 ml) and treated with 0.48 gm succinic acid at 25-30° C., and stirred for 30 minutes. The precipitated solid was filtered, washed with 1.0 ml acetone, and solid dried under vacuum yield 1.4 gm of compound VI having HPLC purity 99.86%; chiral purity: 99.93%.

EXAMPLE 4

PREPARATION OF (3R)-1-AZABICYCLO[2.2.2]OCT-3-YL4-NITROPHENYL CARBONATE OF FORMULA (IV);

To a stirred solution of (3R)-quinuclidin-3-ol (1.0 gm) in dichloromethane (10 ml) was added Bis-(4-dinitrophenyl) carbonate (2.87 gm) at 25-30° C. and the resulting brown solution was stirred at ambient temperature till the completion of reaction by HPLC. Dichloromethane was distilled off to get the residue that was diluted with water (10 ml) and was added concentrated hydrochloric acid till pH of the mixture is 1 to 2. The acidic solution was extracted with di-isopropylether (10 ml×2) to separate out the nitro-phenol.

The aqueous layer was then extracted with dichloromethane (20 ml) to separate the compound of formula (IV). The dichloromethane layer comprising the compound of formula (IV) was further mixed with water (10 ml) and pH was adjusted to 9-10 with ammonium hydroxide. The organic layer was then separated, washed with water, dried over sodium sulphate, and concentrated under vacuum to yield (3R)-1-azabicyclo[2.2.2]oct-3-yl-4-nitrophenyl carbonate of formula (IV) as a syrup with around 46% yield (1.07 gm); HPLC purity: 87.27% by HPLC.

EXAMPLE 5

Preparation of Solifenacin Succinate of Formula (VI)

To a stirred solution of (3R)-1-azabicyclo[2.2.2]oct-3-yl-4-nitrophenyl carbonate (1.0 gm) of formula (IV) obtained as per Example 4 in pyridine (5 ml), (1S)-1-phenyl-1,2,3,4-tetrahydroisoquinoline (0.78 gm) was added and the resulting brown solution was stirred for 6 hrs. After completion of the reaction the solvent was distilled off and the residue obtained was diluted with 10 ml water, the pH of the resulting solution was adjusted to 1-2 using the concentrated hydrochloric acid and extracted with di-isopropylether (10 ml×2) to separate out the nitro-phenol.

The aqueous layer was separated and further extracted with dichloromethane (20 ml) and obtained dichloromethane layer was mixed with water (10 ml) and pH of the resulting mixture was adjusted to 9-10 using ammonium hydroxide. Layers were separated, the organic layer was washed with water, dried over sodium sulphate, and concentrated in vacuum to yield the 1.07 gm (89.43%) of compound solifenacin of formula (I) having HPLC purity 97.08% purity

EXAMPLE 6

Preparation of Solifenacin Succinate of Formula (VI)

To a stirred solution of (3R)-quinuclidin-3-ol (Formula II, 100 gm) in dimethylformamide (400 ml), bis-(4-dinitrophenyl)carbonate (Formula III, 285.04 gm) was added with stirring at 25-30° C. under nitrogen atmosphere. The reaction mass was stirred at 25-30° C. for 2-3 hours. After completion of the reaction which was monitored by TLC, (1S)-1-phenyl-1,2,3,4-tetrahydroisoquinoline (Formula V, 171.44 gm) was added to the resultant brown colored reaction solution. The reaction mixture was further stirred at 25-30° C. for 3-4 hrs. After completion of the reaction (by HPLC), the reaction solution was diluted with water (1000 ml) and the pH of the solution was adjusted to 1-2 using concentrated hydrochloric acid. The resulting reaction solution was extracted with diisopropylether (1000 ml×2) to separate the nitro-phenol.

The aqueous layer was then mixed with dichloromethane (1000 ml), the content was stirred, and dichloromethane layer was separated. Aqueous layer was re-extracted with dichloromethane (1000 ml). The combined dichloromethane was distilled off completely to obtain the residue. The residue was dissolved in water (1000 ml) and toluene (1000 ml) was added and the pH of the biphasic mixture was adjusted to 9-10 with ammonium hydroxide. The mixture was stirred and toluene layer was separated and aqueous layer was re-extracted with toluene (1000 ml). The combined toluene layer were washed with water (1000 ml) followed by solution of 0.5% sodium hydroxide (1000 ml×2) and further washed with water (1000 ml). The toluene layer was distilled off completely to obtain the residue which was further dissolved in acetone (800 ml) and toluene 1080 ml). The solution was treated with Succininc acid (88.0 gm) and the mixture obtained was heated at 55-60° C. for 30 min. The mixture was further cooled to 10-15° C., maintained for 60 min and filtered. The product was dried to afford Solifenacin Succinate (Formula VI) as white crystalline solid. Yield of the compound VI 270 gm. HPLC purity: 99.85%: Chiral Purity: 99.99%

EXAMPLE 7

Purification process for Solifenacin Succinate

The wet material obtained from the example 6 was purified to improve chiral and chemical purity. The wet material (270 gm) was dissolved in a mixture of water (700 ml) and toluene (700 ml) and stirred for 15 min. The pH of resulting mixture was adjusted to 9-10 using aqueous ammonia, stirred for 15-20 min and separated organic and aqueous layer. Aqueous layer was re-extracted with toluene (700 ml) and combined with the separated organic layer. The combined organic layer was washed with water (700 ml×2) and distilled off completely to obtain the thick residue. The residue was dissolved in acetone (1600 ml), decolorized with activated charcoal, and treated with succininc acid (75.0 gm). The contents were heated at 55-60° C. for 30 min, cooled to 10-15° C., and maintained for 60 min. The crystalline solid obtained was filtered, and dried under vacuum (650-700 mm/Hg to afford Solifenaicn Succinate (Formula VI) as white crystalline solid. Yield: 250 gm (66.6%); HPLC purity: 99.95% and Chiral purity: 100.0%.

We claim:

1. A method for the preparation of (1S)-(3R)-1-azabicylco[2.2.2]oct-3-yl-3,4-dihydro-1-phenyl-2(1H)-isoquinolinecarboxylate (Solifenacin), of formula (I) or its pharmaceutically acceptable salts

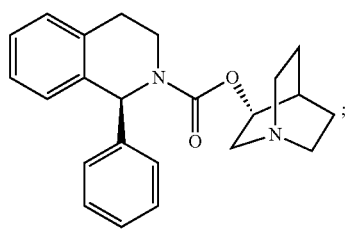

Formula I the method comprising:
a. reacting (R)-quinuclidin-3-ol a compound of formula (II) with bis (aryl) carbonate of formula (IIIa), optionally in the presence of a base, to form (3R)-1-azabicyclo[2.2.2]oct-3-yl-4-nitrophenyl carbonate of formula (IVa)

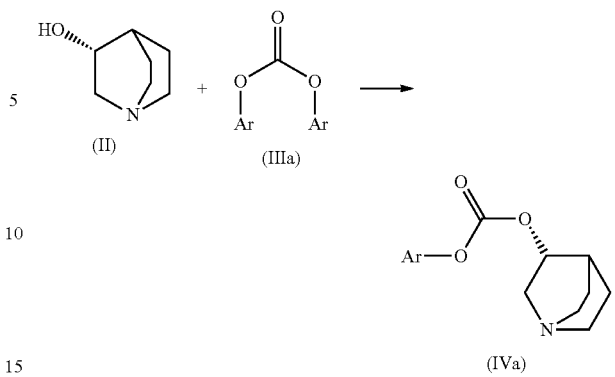

wherein Ar is phenyl, or a substituted phenyl selected from the group consisting of p-nitrophenyl, 4-(trifluoromethyl) phenyl, 4-cyano phenyl, ethyl benzoate, and benzoic acid,
optionally, isolating the compound of formula (IVa); and
b. treating the reaction mixture comprising the formula (IVa) obtained from step (a) or optionally, after isolating the compound of formula (IVa) with (1S)-1-phenyl-1, 2, 3, 4-tetrahydro isoquinoline of formula (V) to obtain the compound of Formula (I), and optionally converting the base into its pharmaceutically acceptable salts

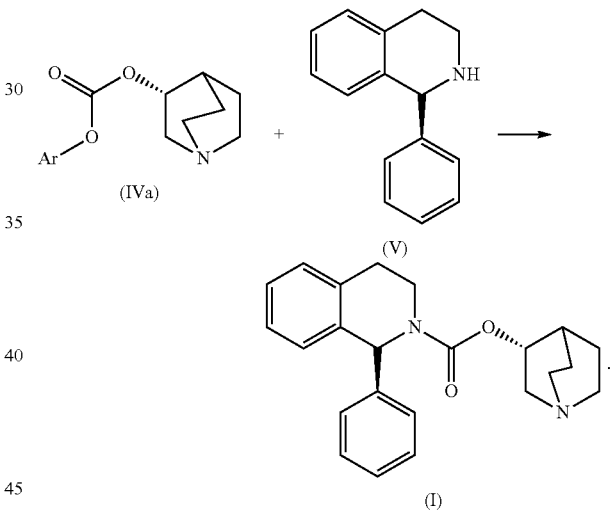

2. The method of claim 1 wherein step (a) is carried out in an organic solvent selected from the group consisting of C1-C10 ether, C5-C8 cyclic ether, C2-10 aliphatic ester, C2-C8 aliphatic amides, sulfoxide, C5-C8 cyclic amines, C5-C10 aliphatic amines, C1-C8 chlorinated hydrocarbon, and mixtures of thereof and in an inert atmosphere at a temperature in the range of −40 to 100° C.

3. The method of claim 1, wherein step (a) is carried out in the presence of an organic base selected from the group consisting of Pyridine, triethylamine, and diethylamine, or an inorganic base selected from the group consisting of alkalimetal carbonates, alkalimetal bicarbonates, alkalimetal hydroxides, and ammonium carbonate.

4. The method of claim 1, wherein step (b) is carried out in an organic solvent and in an inert atmosphere at temperature in the range of −20 to 50° C.

5. The method of claim 1, further comprising:
a. isolating the compound of formula (IVa) from the reaction mixture obtained in step (a); and
b. reacting the compound of formula (IVa) with the compound of formula (V) to form the compound of formula (I).

6. The method as claimed in step (a) of claim 5 wherein the isolation step comprises:
   a. separating out the aryl alcohol from the reaction mixture obtained from step (a) by distilling the organic solvent under vacuum from the reaction mixture of step (a) to get residue, adding water to the residue, adjusting the pH of the resultant mixture to 1 to 2 using an acid, extracting the reaction mixture with a water immiscible organic solvent selected from the group consisting of esters, ethers, hydrocarbons, and mixtures of thereof to separate out aryl alcohol;
   b. isolating the compound of formula (IVa) by extracting the aqueous layer obtained from step (1) with a water immiscible organic solvent selected from the group consisting of esters, ethers, hydrocarbons, chlorinated hydrocarbons and mixtures of thereof to separate the compound of formula (IVa), diluting the organic layer comprising the compound of formula (IVa) with water, adjusting pH of the resulting mixture to 9 to 13, using base, separating the organic layer, washing with water, and then concentrating to yield compound of Formula (IVa) as a syrup.

7. The method of claim 1 further comprising isolation of the compound of formula (I) by:
   1. separating the aryl-alcohol from the reaction mass obtained from step (b) by adding water to the reaction mass followed by adjusting the pH to 1-2 by using acid, adding a water immiscible organic solvent selected from the group consisting of ethers, hydrocarbons, and mixtures of thereof to the reaction mass, followed by mixing, separating the water immiscible organic layer and the aqueous layer comprising the salt of the compound of formula (I); and
   2. isolating the compound of formula (I) by extracting the salt of the compound of formula (I) in a water immiscible organic solvent selected from the group consisting of ethers, hydrocarbons, chlorinated hydrocarbons and mixtures of thereof from the aqueous layer obtained from step (1), adding water to the organic layer or distilling off the solvent from the organic layer to obtain a residue, dissolving the residue in a mixture of water and the water immiscible organic solvent; followed by adjusting the pH of the solution to 9 to 13 by adding base followed by separating the organic layer; washing the organic layer with water, optionally followed by washing with solution of 0.5% of sodium hydroxide and concentrating the organic layer to yield the compound of the formula (I) as syrup/oil.

8. The method of claim 7 wherein the water immiscible organic solvent is selected from the group consisting of diethyl ether, diisopropylether, methyl-tert-butylether, toluene, xylene, heptane, pentane, cyclohexane, dichloromethane, dichlorethane, chloroform, and mixtures of thereof.

9. The method of claim 1, wherein the compound of formula (IIIa) is selected from the group consisting of diphenyl carbonate, bis(p-nitrophenyl)carbonate, bis[4-(trifluoromethyl)phenyl] carbonate, bis(4-cyanophenyl) carbonate, diethyl 4,4'-[carbonylbis(oxy)]dibenzoate, or 4,4'-[carbonylbis(oxy)]dibenzoic acid and the compound of formula (IVa) comprises (3R)-1-azabicyclo[2.2.2]oct-3-yl 4-phenyl carbonate, (3R)-1-azabicyclo[2.2.2]oct-3-yl 4-nitro phenyl carbonate, (3R)-1-azabicyclo[2.2.2]oct-3-yl 4-4-(trifluoromethyl)phenyl carbonate, (3R)- 1-azabicyclo[2.2.2]oct-3-yl 4-cyano phenyl carbonate, (3R)-1-azabicyclo[2.2.2]oct-3-yl 4-ethyl benzoate carbonate, or (3R)-1-azabicyclo[2.2.2]oct-3-yl 4-benzoic acid carbonate.

10. The method of claim 1, wherein formula (IIIa) comprises bis(p-nitrophenyl)carbonate of formula (III)

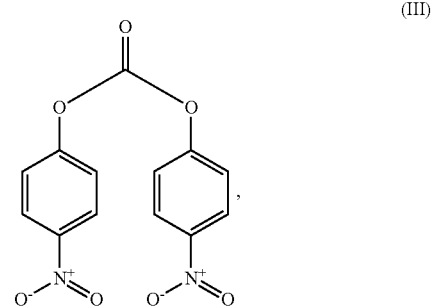

and formula (IVa) comprises (3R)-1-azabicyclo[2.2.2]oct-3-yl 4-phenyl carbonate of formula (IV)

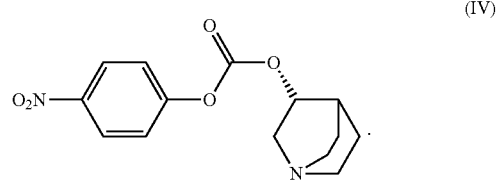

11. The method of claim 1, wherein the compound of formula (II) comprises (R)-, (S)- and (RS)-Quinuclidin-3-ol and the compound of formula (V) comprises (R)-, (S)- and (RS)-1-phenyl-1,2,3,4-tetrahydroisoquinoline to provide the compounds of formula (I), (1R, 3S)-1-azabicyclo [2.2.2] Oct-3-yl-3,4-dihydro-l-phenyl-2(1H)-isoquinoline carboxylate of formula (Ia), (1R, 3R)-1-azabicyclo[2.2.2]Oct-3-yl-3,4-dihydro-1-phenyl-2(1H)-isoquinoline carboxylate of formula (Ib), and (1S, 3S)- 1-azabicyclo[2.2.2]Oct-3-yl-3,4-dihydro-1-phenyl-2(1H)-isoquinoline carboxylate of formula (Ic)

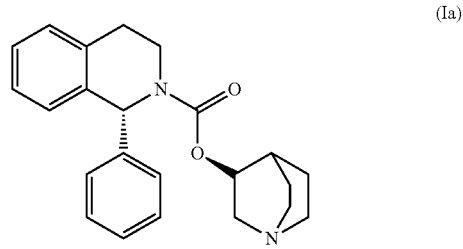

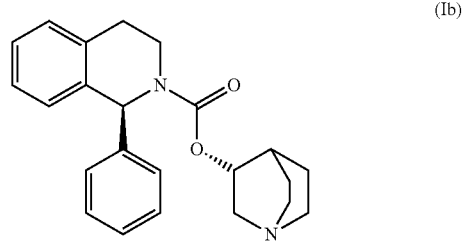

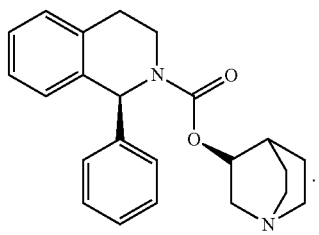

12. A compound (3R)-1-azabicyclo[2.2.2]oct-3-yl 4-aryl carbonate of formula (IVa)

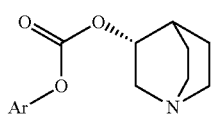

Formula-IVa wherein Ar is phenyl, or substituted phenyl selected from p-nitro phenyl, 4-(trifluoro methyl) phenyl, 4-cyano phenyl, ethyl benzoate, and benzoic acid as an intermediate of Solifenacin.

13. A process for the preparation of the compound of claim 12, the process comprising:

a. reacting (R)-quinuclidin-3-olof formula (II)

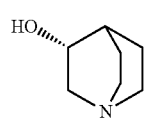

Formula-II with bis (aryl) carbonate of formula (IIIa)

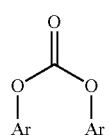

Formula-IIIa wherein Ar is phenyl, or substituted phenyl selected from p-nitro phenyl, 4-(trifluoro methyl) phenyl, 4-cyano phenyl, ethyl benzoate, and benzoic acid,to form (3R)-1-azabicyclo[2.2.2]oct-3-yl 4-aryl carbonate of formula (IVa); and b. isolating the compound of the formula (IVa).

14. The process of claim 13, wherein step (a) is carried out in an organic solvent selected from the group consisting of C1-C10 ether, C5-C8 cyclic ether, C2-10 aliphatic ester, C2-C8 aliphatic amides, sulfoxide, C5-C8 cyclic amines, C5-C10 aliphatic amines, C1-C8 chlorinated hydrocarbon, and mixtures of thereof and in an inert atmosphere at a temperature in the range of −40 to 100° C.

15. The process of claim 13, wherein the compound of formula (IVa) is isolated by 1. separating the aryl alcohol from the reaction mixture obtained from step (a) by distilling the organic solvent under vacuum from the reaction mixture to get a residue, adding water to the residue, adjusting the pH of the resultant mixture to 1 to 2 using an acid, extracting the reaction mass with a water immiscible organic solvent selected from the group consisting of esters, ethers, hydrocarbons, and mixtures of thereof to separate the nitro-phenol; and 2. extracting the aqueous layer obtained from step (1) with a water immiscible organic solvent selected from the group consisting of esters, ethers, hydrocarbons, chlorinated hydrocarbons and mixtures of thereof to separate the compound of formula (IVa), diluting the organic layer with water, adjusting the pH of the resulting mixture to 9 to 13, separating the organic layer, washing with water, and then concentrating to yield compound of Formula (IVa) as a syrup.

16. A method comprising reacting a bis(aryl)carbonate of formula (IIIa) and a (R)-quinuclidin-3-ol compound of formula (II)to form a (3R)-1-azabicyclo[2.2.2]oct-3-yl 4-aryl carbonate of formula (IVa)

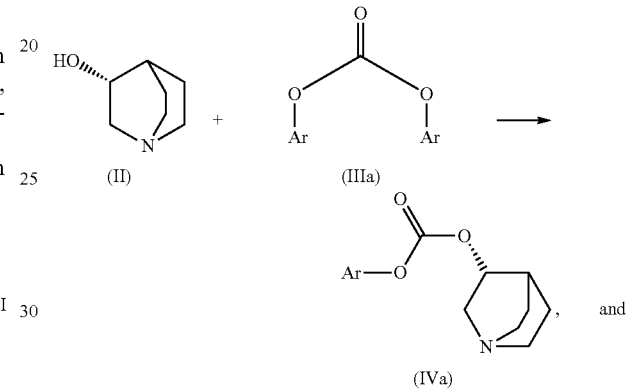

using the (3R)-1-azabicyclo[2.2.21]oct-3-yl 4-aryl carbonate of formula (IVa)as an intermediate in preparation of Solifenacin.

17. The method of claim 16, further comprising treating the (3R)-1-azabicyclo[2.2.2]oct-3-yl 4-aryl carbonate of formula (IVa) with a (1S)-1-phenyl-1,2,3,4-tetrahydro isoquinoline of formula (V)

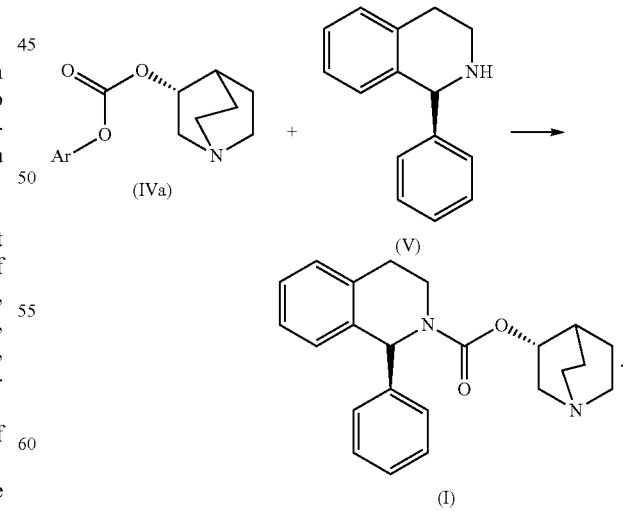

to prepare a Solifenacin of formula (I) or its pharmaceutically acceptable salts.

* * * * *

UNITED STATES PATENT AND TRADEMARK OFFICE
CERTIFICATE OF CORRECTION

PATENT NO.         : 8,283,470 B2                                    Page 1 of 1
APPLICATION NO.    : 13/255561
DATED              : October 9, 2012
INVENTOR(S)        : Vijayvitthal Thippannachar Mathad et al.

It is certified that error appears in the above-identified patent and that said Letters Patent is hereby corrected as shown below:

Claim 16, Column 30, line 35, please change -- [2.2.21] -- to -- [2.2.2] --.

Signed and Sealed this
Twenty-second Day of January, 2013

David J. Kappos
*Director of the United States Patent and Trademark Office*